United States Patent
Kang et al.

(10) Patent No.: US 9,115,974 B2
(45) Date of Patent: Aug. 25, 2015

(54) MOTION-COMPENSATED OPTICAL COHERENCE TOMOGRAPHY SYSTEM

(75) Inventors: Jin U. Kang, Ellicott City, MD (US); Yong Huang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 200 days.

(21) Appl. No.: 13/618,810

(22) Filed: Sep. 14, 2012

(65) Prior Publication Data

US 2014/0078512 A1  Mar. 20, 2014

(51) Int. Cl.
*G01B 11/02*  (2006.01)
*G01B 9/02*  (2006.01)
*A61B 5/00*  (2006.01)

(52) U.S. Cl.
CPC .......... *G01B 9/02076* (2013.01); *A61B 5/0066* (2013.01); *A61B 5/6886* (2013.01); *G01B 9/0205* (2013.01); *G01B 9/02054* (2013.01); *G01B 9/02068* (2013.01); *G01B 9/02091* (2013.01); *A61B 5/721* (2013.01)

(58) Field of Classification Search
CPC .... A61B 3/102; A61B 5/0066; A61B 5/6886; G01B 9/02076; G01B 9/02091; G01B 9/02054; G01B 9/0205; G01B 9/02057; G01B 9/02085; G01B 9/02087; G01N 21/4795; G01N 2021/1787
USPC ................................................. 356/479, 497
See application file for complete search history.

(56) References Cited

U.S. PATENT DOCUMENTS 6,293,674 B1 * 9/2001 Huang et al. ................... 351/221
7,365,856 B2 * 4/2008 Everett et al. .................. 356/479

(Continued)

FOREIGN PATENT DOCUMENTS

JP         4354601 B2   10/2009
WO   WO-2006077107 A1   7/2006

(Continued)

OTHER PUBLICATIONS

Ahmad et al., "Cross-correlation-based image acquisition technique for manually-scanned optical coherence tomography," Opt. Express 17(10), 8125-8136 (2009).

(Continued)

*Primary Examiner* — Michael A Lyons
*Assistant Examiner* — Violeta A Prieto
(74) *Attorney, Agent, or Firm* — Venable LLP; Henry J. Daley; Laura G. Remus

(57) ABSTRACT

A motion-compensated optical coherence tomography system includes an optical coherence tomography sensor that includes a common-path optical fiber having an end for emitting light, reflecting reference light and receiving returned light for detection; a motion-compensation system attached to the common-path optical fiber and operable to move at least a portion of the optical fiber so as to compensate for motion between the end of the common-path optical fiber and an object being imaged; and a feedback control system configured to communicate with the optical coherence tomography sensor and the motion-compensation system. The feedback control system is configured to receive information concerning a measured distance of the end of the common-path optical fiber from the object and provide instructions to the motion-compensation system to decrease an amount of deviation of the measured distance from a desired distance.

14 Claims, 7 Drawing Sheets

(56) References Cited

U.S. PATENT DOCUMENTS

| | | | |
|---|---|---|---|
| 7,755,769 B2* | 7/2010 | Everett et al. | 356/497 |
| 8,711,366 B2* | 4/2014 | Everett et al. | 356/497 |
| 2005/0029978 A1 | 2/2005 | Oleynikov et al. | |
| 2007/0076217 A1 | 4/2007 | Baker et al. | |
| 2009/0141237 A1* | 6/2009 | Izatt et al. | 351/211 |
| 2009/0196477 A1 | 8/2009 | Cense et al. | |
| 2009/0287376 A1* | 11/2009 | Aso | 701/42 |
| 2011/0267340 A1* | 11/2011 | Kraus et al. | 345/419 |
| 2013/0123759 A1* | 5/2013 | Kang et al. | 606/1 |
| 2013/0128267 A1* | 5/2013 | Kang et al. | 356/326 |
| 2014/0063225 A1* | 3/2014 | Kang et al. | 348/79 |

FOREIGN PATENT DOCUMENTS

| | | |
|---|---|---|
| WO | WO-2011139895 A1 | 11/2011 |
| WO | WO-2012/012540 A2 | 1/2012 |

OTHER PUBLICATIONS

Becker et al., "State estimation and feedforward tremor suppression for a handheld micromanipulator with a Kalman filter," IEEE/RSJ, International Conference on Intelligent Robots and Systems, 5160-6165(2011).
Boppart et al., "Forward-imaging instruments for optical coherence tomography," Opt. Lett. 22 (21), 1618-1620 (1997).
Boppart et al., "Optical coherence tomography: feasibility for basic research and image-guided surgery of breast cancer," Breast Cancer Res. Treatment 84(2), 85-97(2004).
Boppart et al., "Intraoperative assessment of microsurgery with three-dimensional optical coherence tomography," Radiology, vol. 208, pp. 81-86, 1998.
Chen et al., "Noninvasive imaging of in vivo blood flow velocity using optical Doppler tomography," Opt. Lett. 22(14), 1119-1121(1997).
Duncan et al., "Processing algorithms for tracking speckle shifts in optical elastography of biological tissues, " J. Biomed. Opt. 6(4), 418-426(2001).
Ha et al., "Compensation of motion artifacts in catheter-based optical frequency domain imaging," Opt. Express 18(11), 11418-11427 (2010).
Han et al., "Handheld forward-imaging needle endoscope for ophthalmic optical coherence tomography inspection, " J. Biomed. Opt. 13(2), 020505(2008).
Huang et al., "Motion compensated fiber-optic confocal microscope based on a common-path optical coherence tomography distance sensor," Opt. Eng. 50(8), 083201 (2011).
Huang et al., "Noncontact common-path Fourier domain optical coherence tomography method for in vitro intraocular lens power measurement", J. Biomed. Opt. 16(12), 126005(2011).
Huang et al., "Real-time 3D and 4D Fourier domain Doppler optical coherence tomography based on dual graphics processing units," Biomed. Opt. Express 3(9), 2162-2174 ( 2012).
Huang et al., "Optical coherence tomography," Science, vol. 254, pp. 1178-1181, 1991.
Huber et al., "Buffered Fourier domain mode locking: unidirectional swept laser sources for optical coherence tomography imaging at 370,000 lines/s," Opt. Lett., vol. 31, pp. 2975-2977, 2006.
Huo et al., "Forward-viewing resonant fiber-optic scanning endoscope of appropriate scanning speed for 3D OCT imaging," Opt. Express 18(14),14375-14384(2010).
Iftimia et al., "Adaptive ranging for optical coherence tomography," Opt. Express 12(17), 4025-4034 (2004).
Jafri et al., "Optical coherence tomography guided neurosurgical procedures in small rodents," J. Neurosci. Methods 176(2), 85-89 (2009).
Jung et al. "Three-dimensional optical coherence tomography employing a 2-axis microelectromechanical scanning mirror," IEEE J. Sel. Top. Quantum Electron. 11(4), 806-810(2005).
Kang et al., "Endoscopic functional Fourier domain common path optical coherence tomography for microsurgery," IEEE J. Sel. Top. Quantum Electron. 16(4), 781-792(2010).
Kang et al., "Real-time three-dimensional Fourier-domain optical coherence tomography video image guided microsurgeries," J. Biomed. Opt. 17(8), 081403 (2012).
Klein et al., "Megahertz OCT for ultrawide-field retinal imaging with a 1050nm Fourier domain mode-locked laser," Opt. Express, vol. 19, pp. 3044-3062, 2011.
Lee et al., "Motion correction for phase-resolved dynamic optical coherence tomography imaging of rodent cerebral cortex, " Biomed. Opt. Express 19(22), 21258-21270 (2012).
Leitgeb et al., "Ultrahigh resolution Fourier domain optical coherence tomography," Opt. Express 12(10), 2156-2165(2004).
Liu et al., "Distortion-free freehand-scanning OCT implemented with real-time scanning speed variance correction," Opt. Express 20(15), 16567-16583 (2012).
Maguluri et al., "Three dimensional tracking for volumetric spectral-domain optical coherence tomography," Opt. Express 15(25), 16808-16817 ( 2007).
Potsaid et al., "Ultrahigh speed Spectral / Fourier domain OCT ophthalmic imaging at 70,000 to 312,500 axial scans per second," Opt. Express, vol. 16, pp. 15149-15169, 2008.
Singh et al., "Physiological tremor amplitude during retinal microsurgery," Proc. 28th Annual Conf. IEEE Eng. Med. Bio. Soc.,171-172(2002).
Tan et al., "In-fiber common-path optical coherence tomography using a conical-tip fiber," Opt. Express 17(4),2375-2380(2009).
Vakhtin et al., "Common-path interferometer for frequency-domain optical coherence tomography," App. Opt. 42(34), 6935-6958 (2003).
Zhang et al., "Common-path low-coherence interferometry fiber-optic sensor guided microincision," J. Biomed. Opt. 16(9),095003(2011).
Zhang et al., "Real-time intraoperative 4D full-range FD-OCT based on the dual graphics processing units architecture for microsurgery guidance," Biomed. Opt. Express. 2(4), 764-770 (2011).
Zysk et al. "Optical coherence tomography: a review of clinical development from bench to bedside," J. Biomed. Opt. 12(5), 051403 (2007).
Potsaid et al., "Ultrahigh Speed 1050 nm Swept Source/Fourier Domain OCT Retinal and Anterior Segment Imaging at 100,000 to 400,000 Axial Scans per Second." *Optics Express* 18.19 (2010): 20029.
Oh et al., "400 KHz Repetition rate Wavelength-Swept Laser and Application to High-Speed Optical Frequency Domain Imaging." *Optics Letters*, vol. 35, No. 7 (Sep. 1, 2010).
Wieser et al., "Multi-Megahertz OCT: High Quality 3D Imaging at 20 million A-scans and 4.5 Gvoxels per Second." *Optics Express* vol. 18, No. 14 (Jul. 2010).
Zhang et al., "A Surface Topology and Motion Compensation System for MicrosurgeryGuidance and Intervention Based on Common-Path Optical Coherence Tomorgraphy." *IEEE Transactions on Biomedical Engineering.* vol. 56, No. 9 (Sep. 2009).
Hillman et al., "Common approach for compensation of axial motion artifacts in swept-source OCT and dispersion in Fourier-domain OCT," Optics Express, 2012.
Kim et al., "Enhancement of common-path fourier domain optical coherence tomography using active surface tracking algorithm," Transcations of the Korean Institute, 2012 (Abstract).
Zhang et al., "A common-path optical coherence tomography distance-sensor based surface tracking and motion compensation handheld microsurgical tool," Progress in Biomedical Optics and Imaging, 2011.
International Search Report and Written Opinion issued in International Application No. PCT/US2013/059736 dated Dec. 20, 2013.

* cited by examiner

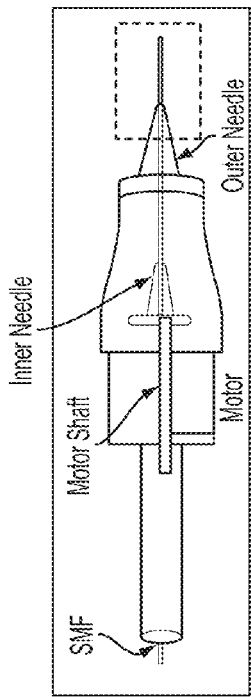
FIG. 1B
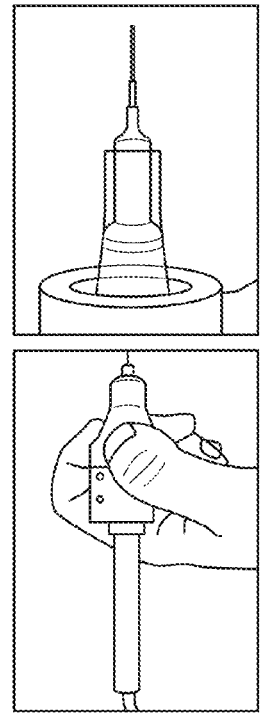
FIG. 1C
FIG. 1D
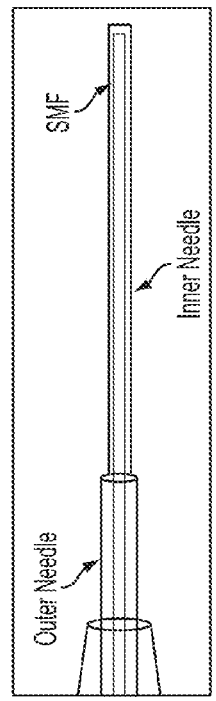
FIG. 1E
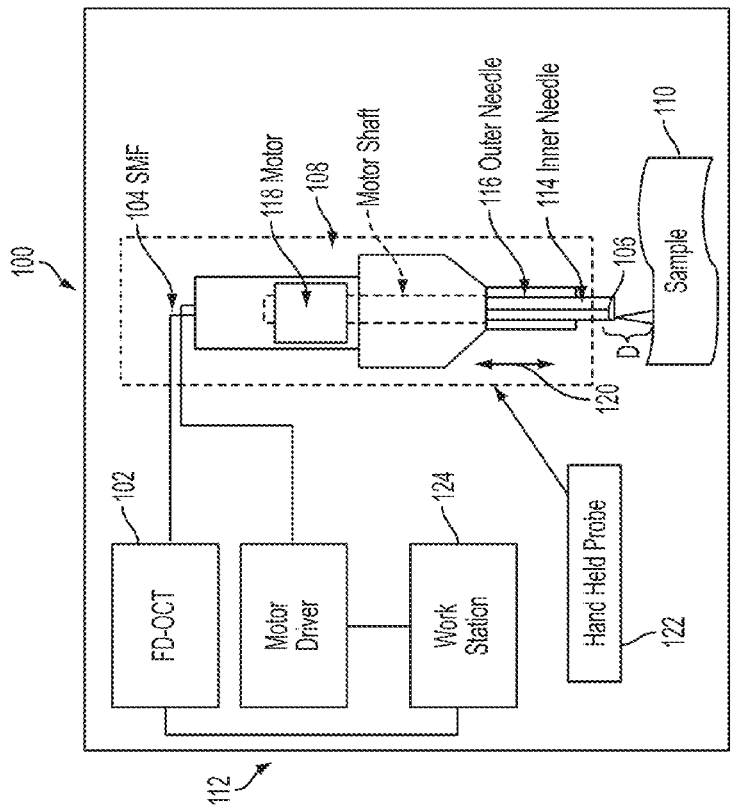
FIG. 1A

MOTION-COMPENSATED OPTICAL COHERENCE TOMOGRAPHY SYSTEM

FEDERAL FUNDING

This invention was made with Government support of Grant No. 1R01EY021540-01A1, awarded by the Department of Health and Human Services, The National Institutes of Health (NIH). The U.S. Government has certain rights in this invention.

BACKGROUND

1. Field of Invention

The field of the currently claimed embodiments of this invention relates to optical coherence tomography systems, and more particularly to motion-compensated optical coherence tomography systems.

2. Discussion of Related Art

Optical coherence tomography (OCT) has been viewed as an "optical analogy" of ultrasound sonogram (US) imaging since its invention in early 1990's (D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical coherence tomography," Science, vol. 254, pp. 1178-1181, 1991). Compared to the conventional image-guided interventions (IGI) using modalities such as magnetic resonance imaging (MRI), X-ray computed tomography (CT) and ultrasound (US) (T. Peters and K. Cleary, *Image-Guided Interventions: Technology and Applications*, Springer, 2008), OCT has much higher spatial resolution and therefore possesses great potential for applications in a wide range of microsurgeries, such as vitreo-retinal surgery, neurological surgery and otolaryngologic surgery.

As early as the late 1990's, interventional OCT for surgical guidance using time domain OCT (TD-OCT) at a slow imaging speed of hundreds of A-scans/s has been demonstrated (S. A. Boppart, B. E. Bouma, C. Pitris, G. J. Tearney, J. F. Southern, M. E. Brezinski, J. G. Fujimoto, "Intraoperative assessment of microsurgery with three-dimensional optical coherence tomography," *Radiology*, vol. 208, pp. 81-86, 1998). Thanks to the technological breakthroughs in Fourier domain OCT (FD-OCT) during the last decade, ultrahigh-speed OCT is now available at >100,000 A-scan/s. For example, see the following:

B. Potsaid, I. Gorczynska, V. J. Srinivasan, Y. Chen, J. Jiang, A. Cable, and J. G. Fujimoto, "Ultrahigh speed Spectral/Fourier domain OCT ophthalmic imaging at 70,000 to 312,500 axial scans per second," Opt. Express, vol. 16, pp. 15149-15169, 2008.

R. Huber, D. C. Adler, and J. G. Fujimoto, "Buffered Fourier domain mode locking: unidirectional swept laser sources for optical coherence tomography imaging at 370,000 lines/s," Opt. Lett., vol. 31, pp. 2975-2977, 2006.

W-Y. Oh, B. J. Vakoc, M. Shishkov, G. J. Tearney, and B. E. Bouma, ">400 kHz repetition rate wavelength-swept laser and application to high-speed optical frequency domain imaging," Opt. Lett., vol. 35, pp. 2919-2921, 2010.

B. Potsaid, B. Baumann, D. Huang, S. Barry, A. E. Cable, J. S. Schuman, J. S. Duker, and J. G. Fujimoto, "Ultrahigh speed 1050 nm swept source/Fourier domain OCT retinal and anterior segment imaging at 100,000 to 400,000 axial scans per second," Opt. Express, vol. 18, pp. 20029-20048, 2010.

W. Wieser, B. R. Biedermann, T. Klein, C. M. Eigenwillig, and R. Huber, "Multi-Megahertz OCT: High quality 3D imaging at 20 million A-scans and 4.5 GVoxels per second," Opt. Express, vol. 18, pp. 14685-14704, 2010.

T. Klein, W. Wieser, C. M. Eigenwillig, B. R. Biedermann, and R. Huber, "Megahertz OCT for ultrawide-field retinal imaging with a 1050 nm Fourier domain mode-locked laser," Opt. Express, vol. 19, pp. 3044-3062, 2011.

For a spectrometer-based SD-OCT, an ultrahigh speed CMOS or CCD line scan camera based system has achieved up to 312,500 line/s in 2008 (Potsaid et al.); while for a swept laser type OCT, >20,000,000 line/s rate was achieved by multi-channel FD-OCT using a Fourier Domain Mode Locking (FDML) laser in 2010 (Wieser et al.).

Fourier-domain optical coherence tomography (FD-OCT) is a high-speed high-resolution three-dimensional imaging modality widely used in biomedical imaging. For OCT to find applications in the interventional imaging area, real-time image processing and display are required.

Optical coherence tomography (OCT) is a non-invasive, high speed, high-resolution, three-dimensional imaging modality that is widely being used for biomedical application [1, 2]. The real-time non-invasive depth-resolved imaging of tissue structure and flow information provided by OCT can be highly valuable information that can assist physicians in making real-time decisions during surgical procedures such as neurosurgery, tumor resection, microvascular anastomosis, and retinal microsurgery [2-10].

In many circumstances, it is more convenient to use a simple hand-held, manually-scanned probe to obtain OCT images of tissues and organs which might otherwise be inaccessible using standard mechanical scanning heads [6]. A hand-held image probe has the following advantages. First, it is small and lightweight, making it easy to access tight spaces. Second, surgeons are intimately familiar with hand-held instruments which can leverage the surgeons' experience and skills with little training. Third, a small hand-held instrument offers greater safety because the surgeon can more easily override or remove the instrument in cases of malfunction [11]. Finally it offers the surgeon great freedom to obtain any image size, for example a larger field-of-view compared to views constrained by apertures of scanning lenses or other endoscopic probes [12-15].

A hand-held probe, however, poses additional challenges over mechanically-rigid scanners. First, non-uniform motion of the probe during lateral manual scanning will cause image distortion and inaccuracy. Earlier work by Ahmed et al. and more recent work by our lab provide solutions to correct non-uniform scanning speed artifact using de correlation of adjacent A-lines [6, 16]. Second, physiological tremor composed of low and high frequency amplitudes over 100 μm [17] would cause large motion artifacts in acquired images. Third, involuntary motions of a subject may also cause OCT imaging artifacts. Finally, the manual scan across and close to the target surface is highly risky—especially involving fragile tissue. For example, in the context of retinal surgery, the retina is only ~350 μm for humans, and tearing them can permanently damage eyesight. Scanning while maintaining a larger distance between the probe tip and target surface is not an ideal solution since that degrades image quality and the imaging depth is typically limited to 3-5 millimeters. While motion is in the form of both axial and lateral directions, axial motion is the primary concern due to its direct effects on the image quality. There have been methods used to compensate for the sample surface topology and axial motion in OCT to keep a good system sensitivity and image range, for example the adaptive ranging technique for time-domain OCT (TDOCT) [18] and the reference mirror tracking method for spectral domain OCT (SDOCT) [19]. Common path optical coherence tomography (CP-OCT) is a simple, all-fiber-based technique that shares reference and probe arm which circumvents group velocity dispersion and polarization compensation [20]. It has been widely investigated for various medical applications [21-24]. CP-OCT has also recently been demonstrated for its effectiveness, simplicity, and integrability for surface topology and motion compensation [25] and smart surgical tools [26]. There thus remains a need for improved optical coherence tomography systems that provide motion compensation.

SUMMARY

A motion-compensated optical coherence tomography system according to an embodiment of the current invention includes an optical coherence tomography sensor that includes a common-path optical fiber having an end for emitting light, reflecting reference light and receiving returned light for detection; a motion-compensation system attached to the common-path optical fiber and operable to move at least a portion of the optical fiber so as to compensate for motion between the end of the common-path optical fiber and an object being imaged; and a feedback control system configured to communicate with the optical coherence tomography sensor and the motion-compensation system. The feedback control system is configured to receive information concerning a measured distance of the end of the common-path optical fiber from the object and provide instructions to the motion-compensation system to decrease an amount of deviation of the measured distance from a desired distance, and the motion-compensated optical coherence tomography system is configured to provide an image from the return light through the common-path optical fiber.

BRIEF DESCRIPTION OF THE DRAWINGS

Further objectives and advantages will become apparent from a consideration of the description, drawings, and examples.

FIG. 1A is a schematic illustration of a motion-compensated optical coherence tomography system according to an embodiment of the current invention.

FIGS. 1B-1E show various views of a prototype of the embodiment of FIG. 1A.

DETAILED DESCRIPTION

Figure 2:
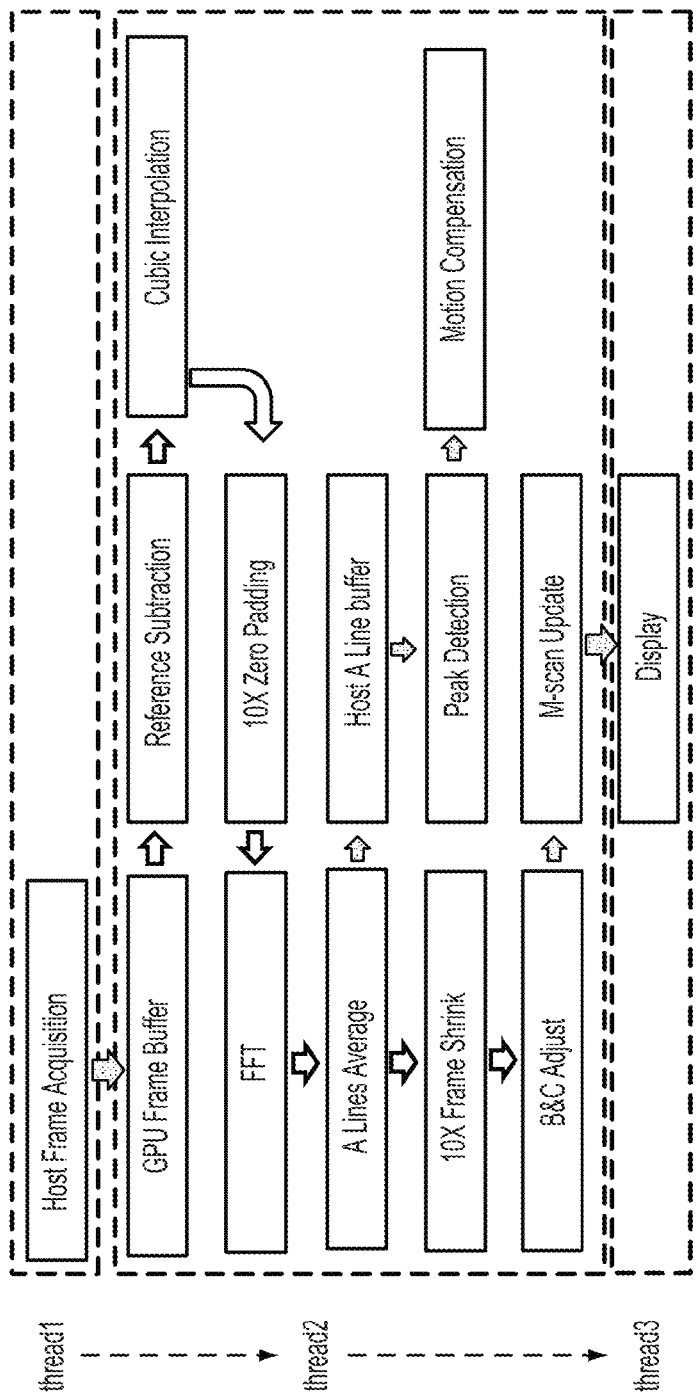
FIG. 2 is a system data processing flowchart: dark, solid arrows indicate data transfer between GPU and host; light, solid arrows indicate processing flow in host; hollow arrows indicate processing flow in GPU; GPU kernel functions are outlined with light lines, and CPU functions are outlined with dark lines; dashed arrows indicate triggering between the three threads.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "light" as used herein is intended to have a broad meaning that can include both visible and non-visible regions of the electromagnetic spectrum. For example, visible, near infrared, infrared and ultraviolet light are all considered as being within the broad definition of the term "light."

The term "real-time" is intended to mean that the OCT images can be provided to the user during use of the OCT system. In other words, any noticeable time delay between detection and image display to a user is sufficiently short for the particular application at hand. In some cases, the time delay can be so short as to be unnoticeable by a user.

A motion-compensated free-hand scanning common-path Fourier-domain optical coherence tomography imaging probe is provided for image guided intervention during microsurgery according to some embodiments of the current invention. In some embodiments, a hand-held needle probe is provided by integrating an imaging fiber probe inside a stainless steel needle which is attached to a ceramic shaft of a piezoelectric motor housed in an aluminum handle. The fiber probe obtains A-scan images. The distance information can be extracted from the A-scans to track the sample surface distance and to maintain a fixed distance using a feedback motor control which effectively compensates hand tremor and target movements in the axial direction. Real-time data acquisition, processing, motion compensation and image saving can be implemented on a customized CPU-GPU hybrid architecture. We performed a 10×zero padding to the raw spectrum to get a 0.16 μm position accuracy with a compensation rate of 460 Hz according to an embodiment of the current invention. In an example, the root-mean-square error of hand-held distance variation from the target position was measured to be 2.93 μm. A cross-correlation maximization based shift correction algorithm can be used for topology correction.

Some embodiments of the current invention can include one or more of the following features:
1. The probe can be small and lightweight. It can allow access to tight spaces.
2. The probe can be flexible. It can allow access to curved spaces
2. The probe can provide the surgeon with freedom to obtain any image size.

3. The probe function can be intuitive and user friendly.
4. The system can compensate for hand tremor and sample motion.
5. The system can prevent accidental damage to an imaging target caused by unexpected motion either from the surgeon or target.
6. A topology correction algorithm can be included to restore sample topology.

FIG. 1A provides a schematic illustration of a motion-compensated optical coherence tomography system 100 according to an embodiment of the current invention that has real-time artifact and saturation correction. The motion-compensated optical coherence tomography system 100 includes an optical coherence tomography sensor 102 that includes a common-path optical fiber 104 having an end 106 for emitting light, reflecting reference light and receiving returned light for detection. The motion-compensated optical coherence tomography system 100 also includes a motion-compensation system 108 attached to the common-path optical fiber 104 and operable to move at least a portion of the optical fiber 104 so as to compensate for motion between the end 106 of the common-path optical fiber 104 and an object 110 being imaged. The motion-compensated optical coherence tomography system 100 further includes a feedback control system 112 configured to communicate with the optical coherence tomography sensor 102 and the motion-compensation system 108.

The feedback control system 112 is configured to receive information concerning a measured distance D of the end 106 of the common-path optical fiber 104 from the object 110 and provide instructions to the motion-compensation system 108 to decrease an amount of deviation of the measured distance D from a desired distance $d_0$. The motion-compensated optical coherence tomography system 100 is configured to provide an image from the return light through the common-path optical fiber 104.

In some embodiments, the optical coherence tomography sensor 102 is a Fourier domain, common path, optical coherence tomography sensor.

In some embodiments, the motion-compensation system 108 can include an inner needle 114 and an outer needle 116 structured such that the inner needle 114 slideably disposed within the outer needle 116. The common-path optical fiber 104 can be disposed within the inner needle 104 with the end 106 of the common-path optical fiber 104 being recessed within the inner needle 114 to avoid contact with the object 110 being imaged.

In some embodiments, the motion-compensation system 108 can include a motor 118 adapted to move the inner needle 114 in an axial direction 120 relative to the outer needle 116 to thereby change a distance D of the end 106 of the common-path optical fiber 104 from the object 110 being imaged in response to the feedback control system 112.

In some embodiments, the motion-compensated optical coherence tomography system 100 can further include a hand piece 122 housing at least a portion of the common-path optical fiber 104 and the motor 118. The hand piece 122 can also be attached to or integral with the outer needle 116 such that the motion-compensated optical coherence tomography system 100 is a free-hand scanning motion-compensated optical coherence tomography system.

In some embodiments, the motion-compensated optical coherence tomography system 100 can further include a data processing system 124 configured to process detection signals from the optical coherence tomography sensor 102 and generate the image. The data processing system 124 can be a workstation, for example. However, the broad concepts of the current invention are not limited to this example. Other data processing systems could be sued according to the particular application. For example, the data processing system could be an application specific system, such as, but not limited to one or more ASICs and/or FPGAs. The data processing system could also be a personal computer, a laptop computer, a tablet computer, etc. It could also be a local or distributed computer, such as a computing system distributed over a local or wide area network, including the interne. The data processing system can also include one or more CPUs for running software and/or one or more graphics processing units (GPUs). In addition to performing image processing, the data processing unit 124 can be configured as part of the feedback control system 112. In some embodiments, the data processing system 124 can perform computation functions for one or more components of the motion-compensated optical coherence tomography system 100.

In some embodiments, the data processing system 124 can be further configured to perform a topological correction of the detection signals. The topological correction of the detection signals can include maximizing a cross correlation between adjacent A-lines of an M-scan image to select a relative axial shift between the adjacent A-lines.

Further additional concepts and embodiments of the current invention will be described by way of the following examples. However, the broad concepts of the current invention are not limited to these particular examples.

EXAMPLES

In the following examples, we demonstrate an example of a CPOCT-based hand-held imaging system capable of motion compensation in the axial direction according to an embodiment of the current invention. A prototype hand-held imaging probe that housed a piezoelectric motor and an imaging fiber tip has been designed and tested. Distance from the fiber tip to the imaging target was monitored and adjusted by the corresponding feedback control of the motor. In principle, the mechanism utilized to compensate axial motion is straightforward based on the teachings herein and similar to adaptive ranging or the reference mirror tracking methods. However, combining this mechanism with a spectral domain CPOCT system by moving the imaging tip solved the problem of degraded lateral resolution with increased imaging depth. Ten times zero-padding of the A-scan spectrum was used to increase the distance sensitivity to 0.16 µm in our system, thus yielding better motion compensation performance. Graphical user interface, real-time data processing, and visualization based on a CPU-GPU hybrid programming architecture were also developed. Hand-held manual scan images of an infrared sensing card, human hand palm and finger nail were obtained. We used a cross-correlation maximization based shift correction algorithm for topology correction to provide anatomically correct images to surgeons, since the system flattens the acquired image. The system was able to track the sample surface with a rate of 460 Hz and the root-mean-square (RMS) error of a hold-still task was measured to be 2.93 µm. To the best of our knowledge, this is the first time that a probe capable of compensating axial motion for image formation in a hand-held manual-scanning OCT has been reported.

Methods

System Configuration

The system configuration and conceptual design of the prototype probe are shown in FIG. 1A. A right angle cleaved single-mode fiber was inserted into an inner needle with a slight recession to protect the fiber end facet. The inner needle was attached to a piezoelectric linear motor. The motor and CP-OCT systems formed a closed-loop control system. A design illustration of the prototype probe used in this study is shown in FIG. 1B (top) and a photograph of the prototype probe is shown in FIG. 1C (center, left). The length of the probe—made of aluminum excluding the needle—is 140 mm; its weight is about 65 g. Such a light weight subjects the surgeon to negligible burden to move it around. A zoomed view of the probe needle set tip is shown in FIG. 1D (center, right) and FIG. 1E (bottom).

We used a fiber pigtailed 635 nm red diode laser (Meshtel, MFM-635-2S) as a guide. Light from a SUPERLUM Broadband Light Source (center wavelength: 878.6 nm, bandwidth: 180 nm) was coupled into a single-mode fiber probe by a 50/50 broadband coupler. The distal end of the single-mode fiber (5.6/125 µm Core/Clad diameter) probe was cleaved at a right angle to provide a Fresnel reflection that served as the reference. The single-mode fiber reference surface was protected by leaving the fiber tip inside the tube. The back-reflected/scattered light from the sample was collected by the bare fiber probe and routed to an in-house-built spectrometer. We used a 12-bit, 2048 pixel CCD line-scan camera (e2v, EM4, USA) with a camera link interface as the detector of the home-built spectrometer. The minimum line period limited by the camera is 14.2 µs, corresponding to a maximum line rate of 70 K A-scans/s. The spectrum data acquired by the camera is transferred to a computer through a frame grabber (National Instruments, PCI-E 1429). In the following experiment, each frame is an average of three A-scans; this was used for tracking the probe tip movement relative to the target surface. The eventual compensation rate of the system was determined by the frame rate of the system, which was less than the maximum line rate. The CP-OCT system has an axial resolution of 3.6 micron in air and 2.8 micron in water. Using the peak detection, we achieved a calibrated position accuracy of 1.6 micron [23]. To further increase the distance-sensing accuracy of the system, we applied the ten times zero-padding technique [27] to achieve a theoretical accuracy of 0.16 micron, sufficient for us to do the motion compensation.

The single-mode fiber probe was then connected to the shaft of a high-speed linear motor (LEGS-L01S-11, Piezo LEGS). We used a quad-core Workstation (DELL, Precision T7500) to obtain the distance information from the CP-OCT signal and deliver commands to the linear motor through a motor driver. The LEGS-L01S-11 has a 35-mm travel range, 20-mm/s maximum speed, less than 1-nm resolution depending on different control modes, and a 10N maximum driving force. For our experiment, we used a motor with a step resolution of 0.2 µm. While A-scans were used to extract distances from the fiber tip to the sample surface, they were also stored to form M-scan images.

Motion Compensation and M-Scan Imaging

During the hand-held operation, voluntary and involuntary movements of the hand and tissue sample causes the distance, D, between the fiber tip and the sample surface to deviate from the desired set-point, $d_0$, which causes a measured error $e=D-d_0$. Based on the measured error, e, a well-known feedback control approach using PID (Proportional, Integral and Derivative) gain was implemented to control the speed of the piezoelectric motor $u_m$ to reduce the error:

$$u_m = K_P e + K_I \int e + K_D \frac{d}{dt} e \quad (1)$$

where $K_P$, $K_I$ and $K_D$ are the proportional, integral and derivative gain coefficients and were empirically optimized. Furthermore, the system can use other types of control schemes to optimize its motion compensation performance.

We performed M-scan imaging while the surface tracking and motion compensation were on. We implemented a real-time, graphical user interface that controls data acquisition, data processing, motion compensation, and image visualization based on a multi-threaded CPU-GPU hybrid programming architecture. The system data processing flowchart is shown in FIG. 2. Thread 1 handled the data acquisition from the spectrometer. Thread 2 performed the data processing and motion compensation. Thread 3 performed the image visualization task. Communication and synchronization between the threads are performed through an event-driven method. Computing tasks were distributed among GPU and CPU to take advantage of both processors. Process steps that can achieve better performance through parallel computing were assigned to GPU (outlined by light boxes), while process steps that require more logical computing were assigned to CPU (outlined by dark boxes). (Thread 1 and 3 were assigned to a CPU. In thread 2, all boxes were assigned to a GPU except for the four further to the lower right hand side in FIG. 2.) After the raw spectrum was transferred to the GPU buffer, it was first subtracted by a pre-acquired physical reference spectrum, and then was cubic interpolated from the λ domain to the k domain. After that, a ten times zero-padding was applied to the interpolated data to increase the distance sensitivity. Three A-scans of post-FFT data of the zero-padded spectrum were averaged to increase the SNR of the A-line data. Due to the ten times zero padding, the post-FFT A-line was shrunk back to normal size and then brightness and contrast adjustment was applied to the shrunken A-line for display purposes. Meanwhile the non-shrunken averaged A-line with higher distance sensitivity was transferred back to the CPU host for the purpose of peak detection and motion compensation. In the following test, the CCD camera was running at 460 fps, which corresponds to a motion compensation rate of 460 Hz with 2.2 ms interval. This gives an effective sampling rate of 460 A-scans per second while the hand is moving the probe.

Topology Correction

Figure 3:
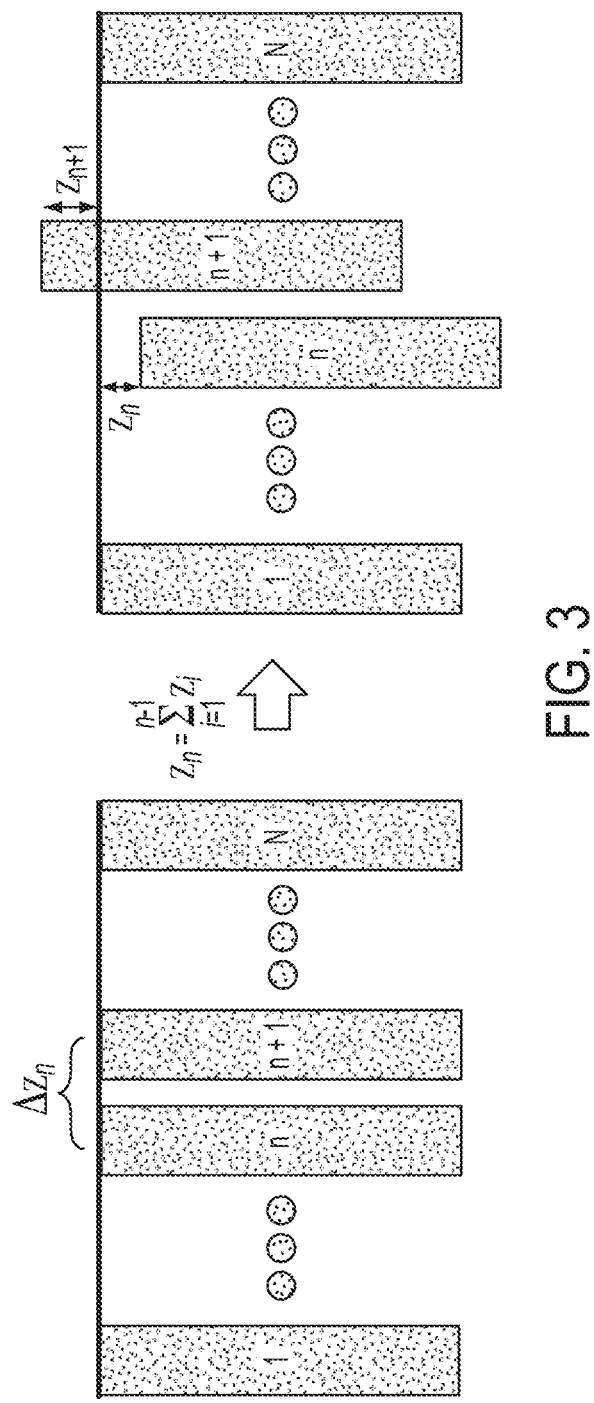
FIG. 3 is a schematic illustration of the cross-correlation maximization-based shift correction algorithm according to an embodiment of the current invention.

The motion compensation function of the probe tries to keep the distance between the imaging fiber tip and sample surface constant during the OCT imaging, which eliminates the motion artifacts due to hand and sample motions, and the sample surface topology. While suppression of the hand and sample motions is what is desired, removal of the surface topology is a side effect that should be addressed. The motion compensation algorithm includes Doppler velocity-based correction [28] and image structure intensity based position correction [29]. In this example, we performed the topology correction by shifting certain number of pixels (Δz) in the axial direction to maximize the cross-correlation between adjacent A-scans for its simplicity and effectiveness. This method was evaluated in [29] for bulk image shifts (BISs) correction. The algorithm is illustrated in FIG. 3. For an image consisting of N A-scans, an array with the size of N−1 containing $\Delta z_n$ will be created. Here, $\Delta z_n$ indicates the pixel-shift amount between A-line (n) and A-line (n+1), while n∈[1, N−1]. Then, using the first A-line as the origin ($Z_1=0$), the total amount of pixel shift Z for A-line n is the summation from $\Delta z_1$ to $\Delta z_{n-1}$, n∈[2, N]. By shifting A-line n with the corresponding $Z_n$ in the axial direction, the final topology correction image is achieved. The assumption for this method working properly is that adjacent A-scans of biological tissue exhibit maximum cross-correlation under a natural topology state, which is intuitive [30] and that they are correlated, which is satisfied by experimentally oversampling the imaging area.

Results and Discussion

Motion Compensation Test

Figure 4A:
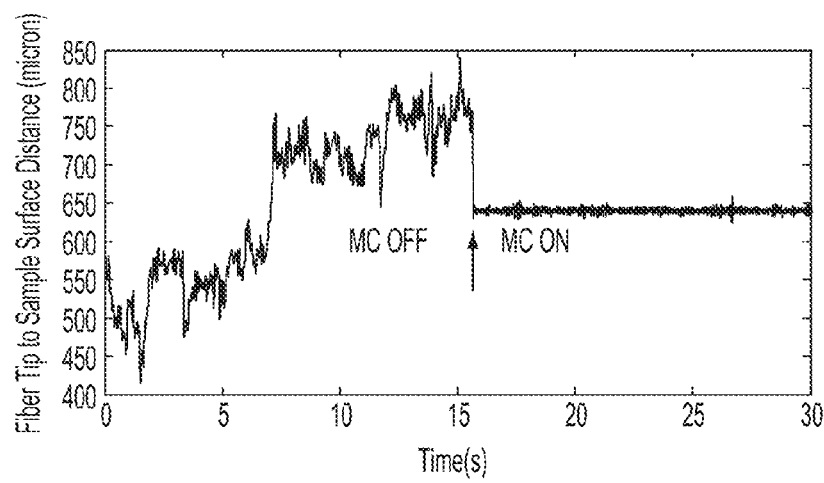
FIGS. 4A-4C show (4A, top) Free hand-held probe position tracking; (4B, middle) zoomed view of motion compensation, time zero corresponding to the arrow position in (4A); (4C, bottom) frequency analysis 0 to 20 Hz: lower (motion compensation is on), upper (motion compensation is off).
Figure 4B:
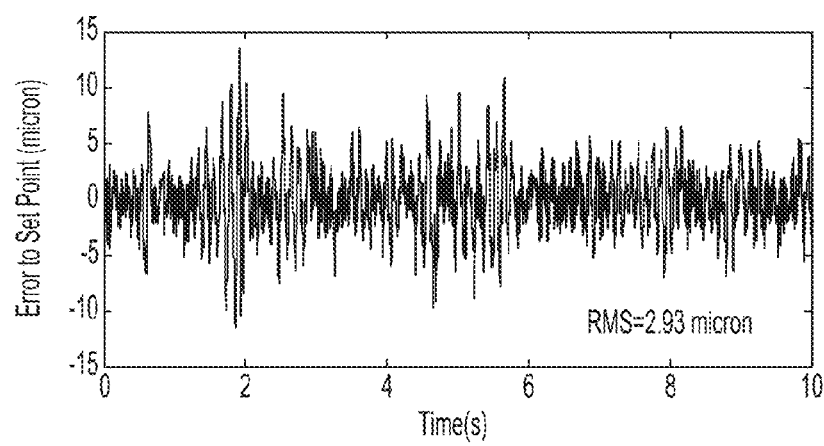
Figure 4C:
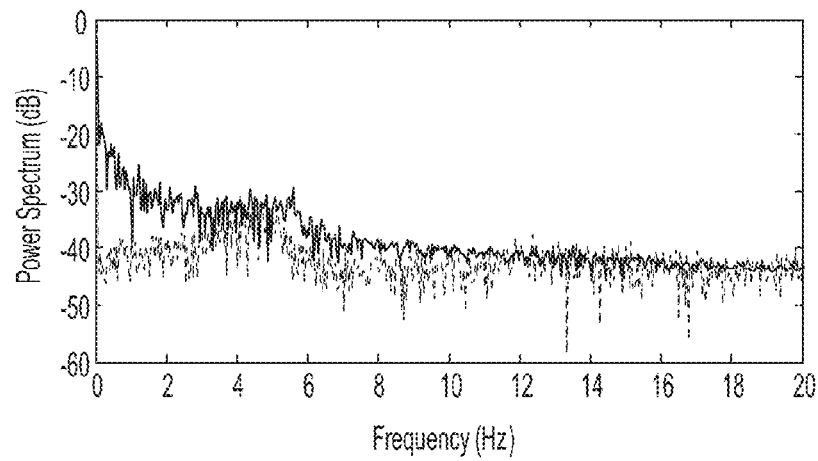

First, we tested the motion compensation function of our system using "hold-still" task. The probe was held by one volunteer and pointed perpendicular to a target surface. The operator tried to maintain a constant distance of D=640 µm and the probe position was recorded as the function of time. As shown in FIG. 4A, our feedback control of the motor greatly reduced the hand tremor which is composed of both low frequency drift and high frequency vibration. The system was able to limit the hold-position drift/error to less than the maximum peak-to-peak error of ±114 µm as shown in FIG. 4B. The RMS error after motion compensation was much lower and was ±13 µm. FIG. 4C shows the frequency spectrum analysis results of the fiber tip-to-probe distance with (lower) and without (upper) motion compensation over a 10-second period. As we can see from the spectrum, the hand tremor has been well compressed.

Hand-Held Imaging

Figure 5A:
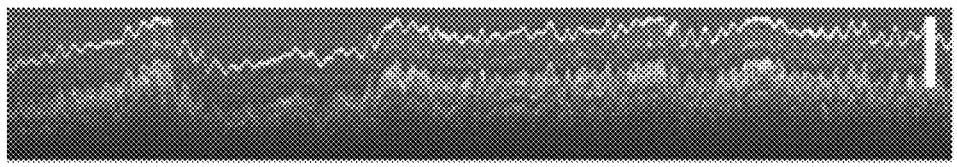
FIGS. 5A-5D show an example of hand-held scanning images of an IR card without (5A, top) and with (5B) motion compensation; (5C) topology correction for (5B); (5D, bottom) standard galvanometer scanning image of IR card composed of 3 separate measurements covering a lateral range of 6 mm (scale bar: 500 μm).
Figure 5B:
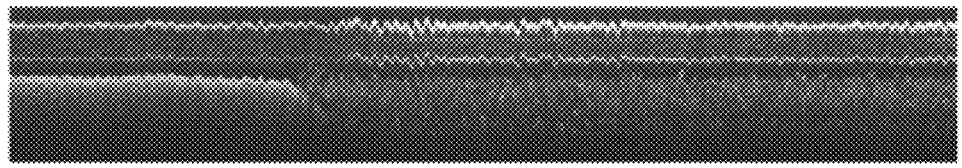
Figure 5C:
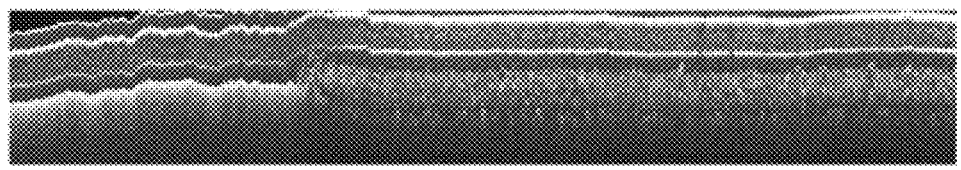
Figure 5D:
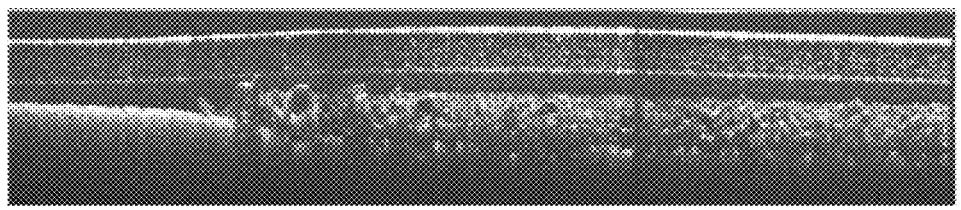
Figure 6A:
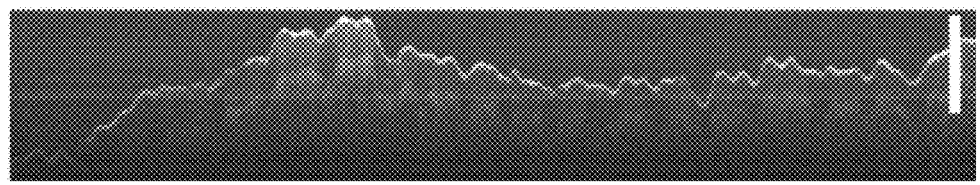
FIGS. 6A-6C show hand-held imaging of human hand palm without (6A, top) and with (6B, middle) motion compensation; (6C, bottom) topology-corrected image for (6B) (scale bar: 500 μm).
Figure 6B:
Figure 6C:
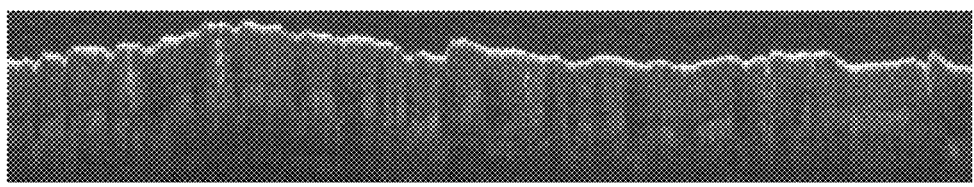

To demonstrate that the motion-compensated hand-held probe can significantly enhance the imaging quality of the free-hand scanning OCT system, we did a series of imaging using an infrared (IR) sensing card and in vivo tissues. Each image consisted of 1000 A-scans. The scanning range and resolution were determined by how fast the lateral scanning was performed. Normally the scanning range was in the order of several millimeters. As can be seen in FIG. 5A (top), the free-hand manual-scanning image of an infrared sensing card degrades due to the hand tremor. A flat surface IR sensor card was distorted into a crooked surface. Meanwhile, as the probe-to-sample surface distance increases the signal intensity decreases, this causes the loss of detailed axial information in the A-scan image. FIG. 5B shows a free-hand manual-scanning image of the same IR card with the motion compensation on. We can clearly see that the acquired IR card image is flat, with much less variation in the signal amplitude compared to FIG. 5A. Moreover, there is no A-scan axial information loss in FIG. 5B. FIG. 5C is the topology-corrected image based on FIG. 5B. We can clearly see that—although not perfect—the surface topology of the IR card has been recovered as the saw-tooth modulated surface has been smoothed. Note that there are still lateral non-uniform scanning speed artifacts over the image. In some embodiments, one can combine the method we used in [16] together with our axial topology correction method. To get a sense of what the true object should be like, we imaged the IR card with a standard galvanometer-controlled scanning mirror pair. The result is shown in FIG. 5D (bottom), which consists of three separate measurements appended together laterally, covering a range of 6 mm.

Figure 7A:
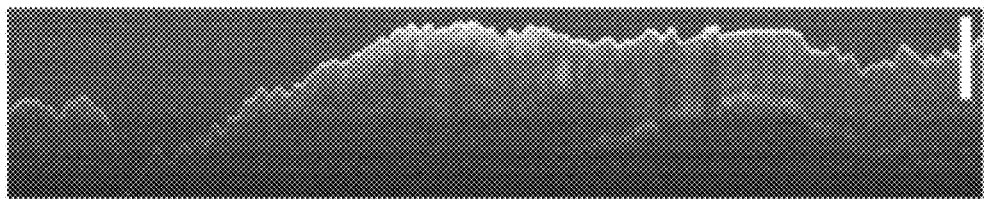
FIGS. 7A-7C show hand-held scanning of human finger nail without (7A, top) and with (7B, middle) motion compensation; (7C, bottom) topology-corrected image for (7B) (scale bar: 500 μm).
Figure 7B:
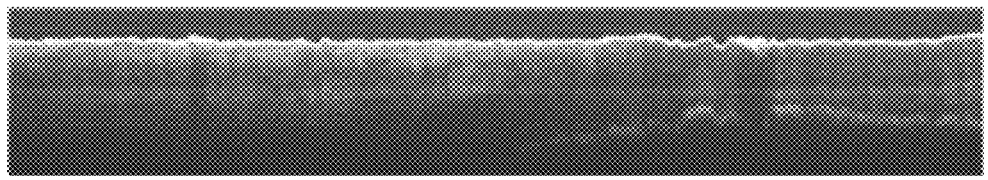
Figure 7C:
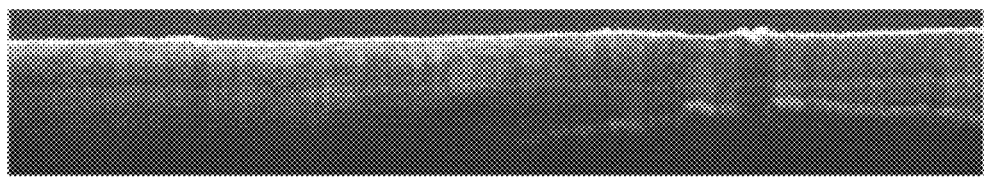

We further tested our system by imaging a non-stationary, naturally placed palm of the hand and finger nail; the results are shown in FIGS. 6A-6C and 7A-7C. The hand tremor is apparent on images without motion compensation, FIG. 6A and FIG. 7A. Accompanied with hand tremor was the non-uniform intensity variation over the scanned images. When the probe distance increases, A-lines become dimmer and sometimes get completely lost. One extreme case is shown in the left part of FIG. 6A and FIG. 7A: the probe is so far away from the tip that detailed structure or anatomy information beneath the target surface was not imaged. The effect of motion compensation can clearly be seen from images FIG. 6B and FIG. 7B. The low frequency axial drift was almost completely negated while the amplitude of high frequency vibration was compressed to less than ±14 µm peak to peak. Detailed structures of the hand palm and finger nail are clearly visible. We can clearly see the boundary between epidermises and dermises layers and sweat duct lying within the epidermises layer. Due to the wavy surface topology of hand palm, the probe compensates more when the hand palm was imaged compared to the finger nail. After surface topology correction, FIG. 6C revealed the smooth wavy surface topology of hand palm clearly, and the sweat duct in FIG. 6C becomes naturally spiral. FIG. 7C also revealed smooth and natural topology of the finger nail junction area. These performances of our system were consistent with the stationary IR card imaging. Safety is one of the main concerns for image-guided intervention. By keeping our probe at a constant distance of 200 µm, risk of damaging the sample surface by accidental hand movement was avoided—an important factor which needs to be addressed during image-guided microsurgery intervention.

Performance of motion compensation is a crucial factor that affects the quality of free-hand scanning OCT systems. In our experiment, we used a piezoelectric motor controlled OCT probe to provide the motion compensation through a USB com port interface with baud rate of 9600 bits/s. Command delivery through USB cable consists of 19 bits: 8 of them are used to control the time cost of one motor step; 10 of them are used to control how many steps to move during one command, while 1 bit of them is the stop bit, which gave us the maximum compensation rate of around 505 Hz. During our experiment, the compensation rate varied from 450 Hz to 470 Hz. We confirmed the compensation rate by continuously sending commands to the motor and recording the time cost in C++ without any other computation task involved. The result was 500 Hz, which corresponds well with the 505-Hz limit. The command delivery latency through the USB port was one of the bottlenecks. Another important factor that affected the motion compensation result was our system distance sensitivity. It is easy to compensate for small errors, but this would require better distance sensitivity that would enable the system to detect these smaller errors. We applied a 10×zero-padding to the spectrum, which effectively improved the system distance sensitivity by a factor of 10: from 1.6 µm to 0.16 µm. However, such a digital processing method cannot improve the system sensitivity indefinitely [27]. As the time-varying M-scan images were recorded, there was a non-uniform spatial sampling rate in the lateral direction due to the non-constant scanning velocity of hand-held scanning. The motion-compensation process results in flat images, which eliminates the topographical information of the target surface, therefore we implemented a simple and intuitive cross-correlation maximization-based shift correction algorithm to restore the target topology.

CONCLUSION

In the above examples according to an embodiment of the current invention, we demonstrated a hand-held, manual-scanning OCT system capable of compensating hand tremor and tracking target surfaces. The exemplar system operates at a compensation rate of 460 Hz with RMS error of 2.93 µm. Images from an IR-card and in vivo hand palm and finger nail were obtained, which showed greatly reduced hand tremor artifacts. We corrected the sample surface topology through a cross-correlation maximization-based shift method. Moreover, the system could significantly reduce the risk of tearing the target surface.

REFERENCES AND LINKS

1. D. Huang, E. A. Swanson, C. P. Lin, J. S. Schuman, W. G. Stinson, W. Chang, M. R. Hee, T. Flotte, K. Gregory, C. A.

1. Puliafito, and J. G. Fujimoto, "Optical coherence tomography," Science, 254(5035), 1178-1181 (1991).
2. B. E. Bouma, *Handbook of Optical Coherence Tomography*, (New York: Marcel Dekker, 2001).
3. A. M. Zysk, F. T. Nguyen, A. L. Oldenburg, D. L. Marks, and S. A. Boppart, "Optical coherence tomography: a review of clinical development from bench to bedside," J. Biomed. Opt. 12(5), 051403 (2007).
4. S. A. Boppart, W. Luo, D. L. Marks, and K. W. Singletary, "Optical coherence tomography: feasibility for basic research and image-guided surgery of breast cancer," Breast Cancer Res. Treatment 84(2), 85-97 (2004).
5. M. S. Jafri, R. Tang, and CM. Tang, "Optical coherence tomography guided neurosurgical procedures in small rodents," J. Neurosci. Methods 176(2), 85-89 (2009).
6. A. Ahmad, S. G. Adie, E. J. Chaney, U. Sharma, and S. A. Boppart, "Cross-correlation-based image acquisition technique for manually-scanned optical coherence tomography," Opt. Express 17(10), 8125-8136 (2009).
7. K. Zhang and J. U. Kang, "Real-time intraoperative 4D full-range FD-OCT based on the dual graphics processing units architecture for microsurgery guidance," Biomed. Opt. Express. 2(4), 764-770 (2011).
8. J. U. Kang, Y. Huang, K. Zhang, Z. Ibrahim, J. Cha, W. P. A. Lee, G. Brandacher and P. L. Gehlbach, "Real-time three-dimensional Fourier-domain optical coherence tomography video image guided microsurgeries," J. Biomed. Opt. 17(8), 081403 (2012).
9. Z. P. Chen, T. E. Milner, S. Srinivas, X. Wang, A. Malekafzali, M. J. C. V. Gernert, and J. S. Nelson, "Noninvasive imaging of in vivo blood flow velocity using optical Doppler tomography," Opt. Lett. 22(14), 1119-1121 (1997).
10. Y. Huang, X. Liu, and J. U. Kang, "Real-time 3D and 4D Fourier domain Doppler optical coherence tomography based on dual graphics processing units," Biomed. Opt. Express 3(9), 2162-2174 (2012).
11. B. C. Becker, R. A. MacLachlan, and C. N. Riviere, "State estimation and feedforward tremor suppression for a handheld micromanipulator with a Kalman filter," IEEE/RSJ, International Conference on Intelligent Robots and Systems, 5160-6165 (2011).
12. S. A. Boppart, B. E. Bouma, C. Pitris, G. J. Tearney, and J. G. Fujimoto, "Forward-imaging instruments for optical coherence tomography," Opt. Lett. 22 (21), 1618-1620 (1997).
13. W. G. Jung, J. Zhang, L. Wang, P. Wilder-Smith, Z. P. Chen, D. T. McCormick, and N. C. Tien, "Three-dimensional optical coherence tomography employing a 2-axis microelectromechanical scanning mirror," IEEE J. Sel. Top. Quantum Electron. 11(4), 806-810 (2005).
14. S. Han, M. V. Sarunic, J. Wu, M. Humayun, and C. H. Yang, "Handheld forward-imaging needle endoscope for ophthalmic optical coherence tomography inspection," J. Biomed. Opt. 13(2), 020505 (2008).
15. L. Huo, J. Xi, Y. Wu, and X. Li, "Forward-viewing resonant fiber-optic scanning endoscope of appropriate scanning speed for 3D OCT imaging," Opt. Express 18(14), 14375-14384 (2010).
16. X. Liu, Y. Huang, and J. U. Kang, "Distortion-free freehand-scanning OCT implemented with real-time scanning speed variance correction," Opt. Express 20(15), 16567-16583 (2012).
17. S. P. N. Singh and C. N. Riviere, "Physiological tremor during retinal microsurgery," Proc. 28th Annual Conf. IEEE Eng. Med. Bio. Soc., 171-172 (2002).
18. N. V. Iftimia, B. E. Bouma, J. F. de Boer, B. H. Park, B. Cense and G. J. Tearney, "Adaptive ranging for optical coherence tomography," Opt. Express 12(17), 4025-4034 (2004).
19. G. Maguluri, M. Mujat, B. H. Park, K. H. Kim, W. Sun, N. V. Iftimia, R. D. Ferguson, D. X. Hammer, T. C. Chen, and J. F. de Boer, "Three dimensional tracking for volumetric spectral-domain optical coherence tomography," Opt. Express 15(25), 16808-16817 (2007).
20. A. Vakhtin, D. Kane, W. Wood and K. Peterson, "Common-path interferometer for frequency-domain optical coherence tomography," App. Opt. 42(34), 6935-6958 (2003).
21. Y. Huang, K. Zhang, J. U. Kang, D. Calogero, R. H. James, I. Ilev, "Noncontact common-path Fourier domain optical coherence tomography method for in vitro intraocular lens power measurement", J. Biomed. Opt. 16(12), 126005 (2011).
22. J. U. Kang, J. H. Han, X. Liu, K. Zhang, C. G. Song and P. Gehlbach, "Endoscopic functional Fourier domain common path optical coherence tomography for microsurgery," IEEE J. Sel. Top. Quantum Electron. 16(4), 781-792 (2010).
23. Y. Huang, K. Zhang, C. Lin, and J. U. Kang, "Motion compensated fiber-optic confocal microscope based on a common-path optical coherence tomography distance sensor," Opt. Eng. 50(8), 083201 (2011).
24. K. M. Tan, M. Mazilu, T. H. Chow, W. M. Lee, K. Taguchi, B. K. Ng, W. Sibbett, C. S. Herrington, C. T. A. Brown and K. Dholakia, "In-fiber common-path optical coherence tomography using a conical-tip fiber," Opt. Express 17(4), 2375-2380 (2009).
25. K. Zhang W. Wang, J. H. Han and J. U. Kang, "A surface topology for microsurgery guidance and intervention based on common-path optical coherence tomography," IEEE Trans. on Biomed. Eng. 56(9), 2318-2321 (2009).
26. K. Zhang and J. U. Kang, "Common-path low-coherence interferometry fiber-optic sensor guided micro-incision," J. Biomed. Opt. 16(9), 095003 (2011).
27. R. Leitgeb, W. Drexler, A. Unterhuber, B. Hermann, T. Bajraszewski, T. Le, A. Stingl and A. Fercher, "Ultrahigh resolution Fourier domain optical coherence tomography," Opt. Express 12(10), 2156-2165 (2004).
28. J. Y. Ha, M. Shishkov, M. Colice, W. Y. Oh, H. Yoo, L. Liu, G. J. Tearney, and B. E. Bouma, "Compensation of motion artifacts in catheter-based optical frequency domain imaging," Opt. Express 18(11), 11418-11427 (2010).
29. J. Lee, V. Srinivasan, H. Radharishnan, and D. A. Boas, "Motion correction for phase-resolved dynamic optical coherence tomography imaging of rodent cerebral cortex," Biomed. Opt. Express 19(22), 21258-21270 (2012).
30. D. D. Duncan and S. J. Kirkpatrick, "Processing algorithms for tracking speckle shifts in optical elastography of biological tissues," J. Biomed. Opt. 6(4), 418-426 (2001).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A motion-compensated optical coherence tomography system, comprising:
    an optical coherence tomography sensor comprising a common-path optical fiber having an end for emitting light, reflecting reference light and receiving returned light for detection;
    a motion-compensation system attached to said common-path optical fiber and operable to move at least a portion of said optical fiber so as to compensate for motion between said end of said common-path optical fiber and an object being imaged;
    a feedback control system configured to communicate with said optical coherence tomography sensor and said motion-compensation system; and
    a data processing system in communication with said optical coherence tomography sensor;
    wherein said feedback control system is configured to receive information concerning a measured distance of said end of said common-path optical fiber from said object and provide instructions to said motion-compensation system to decrease an amount of deviation of said measured distance from a desired distance,
    wherein said motion-compensated optical coherence tomography system is configured to provide a two-dimensional image from said return light through said common-path optical fiber,
    wherein said data processing system is configured to process detection signals from said optical coherence tomography sensor and generate said image,
    wherein said motion-compensation system removes a surface topology of said object in said two-dimensional image, and
    wherein said data processing system is configured to restore said surface topology of said object in said two-dimensional image.

2. A motion-compensated optical coherence tomography system according to claim 1, wherein said motion-compensation system comprises an inner needle and an outer needle, said inner needle being slideably disposed within said outer needle, and
    wherein said common-path optical fiber is disposed within said inner needle with said end of said common-path optical fiber being recessed within said inner needle to avoid contact with said object being imaged.

3. A motion-compensated optical coherence tomography system according to claim 2, wherein said motion-compensation system comprises a motor adapted to move said inner needle in an axial direction relative to said outer needle to thereby change a distance of said end of said common-path optical fiber from said object being imaged in response to said feedback control system.

4. A motion-compensated optical coherence tomography system according to claim 3, further comprising a hand piece housing at least a portion of said common-path optical fiber and said motor, and attached to or integral with said outer needle, such that said motion-compensated optical coherence tomography system is a free-hand scanning motion-compensated optical coherence tomography system.

5. A motion-compensated optical coherence tomography system according to claim 1, wherein said data processing system is configured to restore said surface topology by performing a topological correction of said detection signals.

6. A motion-compensated optical coherence tomography system according to claim 5, wherein said topological correction of said detection signals comprises maximizing a cross correlation between adjacent A-lines of an M-scan image to select a relative axial shift between said adjacent A-lines.

7. A motion-compensated optical coherence tomography system according to claim 4, wherein said data processing system is configured to restore said surface topology by performing a topological correction of said detection signals.

8. A motion-compensated optical coherence tomography system according to claim 7, wherein said topological correction of said detection signals comprises maximizing a cross correlation between adjacent A-lines of an M-scan image to select a relative axial shift between said adjacent A-lines.

9. A motion-compensated optical coherence tomography system according to claim 4, wherein said motor is a piezoelectric motor, and wherein said feedback control system is configured to control speed $u_m$ of said piezoelectric motor to reduce error e=D-do between measured distance D and desired distance do according to the formula $$u_m = K_P e + K_I \int e + K_D \frac{d}{dt} e$$

where $K_P$, $K_I$ and $K_D$ are proportional, integral and derivative gain coefficients, respectively.

10. A motion-compensated optical coherence tomography system according to claim 9, wherein said proportional, integral and derivative gain coefficients $K_P$, $K_I$ and $K_D$ are empirically optimized.

11. A motion-compensated optical coherence tomography system according to claim 8, wherein said motor is a piezoelectric motor, and
    wherein said feedback control system is configured to control speed $u_m$ of said piezoelectric motor to reduce error e=D-$d_0$ between measured distance D and desired distance do according to the formula $$u_m = K_P e + K_I \int e + K_D \frac{d}{dt} e$$

where $K_P$, $K_I$ and $K_D$ are proportional, integral and derivative gain coefficients, respectively.

12. A motion-compensated optical coherence tomography system according to claim 11, wherein said proportional, integral and derivative gain coefficients $K_P$, $K_I$ and $K_D$ are empirically optimized.

13. A motion-compensated optical coherence tomography system according to claim 1, wherein said optical coherence tomography sensor is a Fourier domain, common-path optical coherence tomography sensor.

14. A motion-compensated optical coherence tomography system according to claim 12, wherein said optical coherence tomography sensor is a Fourier domain, common-path optical coherence tomography sensor.

* * * * *